US008540982B2

(12) United States Patent
Sheikh et al.

(10) Patent No.: US 8,540,982 B2
(45) Date of Patent: *Sep. 24, 2013

(54) METHODS FOR INDUCING A NATURAL KILLER (NK) CELL-MEDIATED IMMUNE RESPONSE AND FOR INCREASING NK CELL ACTIVITY

(75) Inventors: Nadeem Sheikh, Seattle, WA (US); Lori Jones, Seattle, WA (US)

(73) Assignee: Dendreon Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/443,703

(22) Filed: Apr. 10, 2012

(65) Prior Publication Data

US 2012/0258476 A1    Oct. 11, 2012

Related U.S. Application Data

(63) Continuation of application No. 12/077,823, filed on Mar. 21, 2008, now Pat. No. 8,153,120.

(60) Provisional application No. 60/896,461, filed on Mar. 22, 2007.

(51) Int. Cl.
*A61K 39/00* (2006.01)
*A61K 35/14* (2006.01)
*G01N 33/48* (2006.01)
*G01N 33/50* (2006.01)

(52) U.S. Cl.
USPC ............... 424/93.71; 424/534; 435/93.71; 435/40.51

(58) Field of Classification Search
None
See application file for complete search history.

(56) References Cited

U.S. PATENT DOCUMENTS

| | | | |
|---|---|---|---|
| 5,232,704 A | 8/1993 | Franz et al. | |
| 5,976,546 A * | 11/1999 | Laus et al. | 424/192.1 |
| 6,120,803 A | 9/2000 | Wong et al. | |
| 6,273,340 B1 | 8/2001 | Rivailler et al. | |
| 6,488,964 B2 | 12/2002 | Bruna et al. | |
| 2004/0197903 A1 * | 10/2004 | Pestano | 435/372 |

FOREIGN PATENT DOCUMENTS

| | | |
|---|---|---|
| WO | WO 98/55107 A1 | 12/1998 |
| WO | WO 01/27245 A2 | 4/2001 |
| WO | WO 03/002101 A1 | 1/2003 |
| WO | WO 03/035040 A1 | 1/2003 |

OTHER PUBLICATIONS

Kanof, 'Preparation of Human Mononuclear Cell Populations and Subpopulations', In: Current Protocols in Immunology, 1991, pp. 7.1.1-7.1.5.*
Ferlazzo et al (Journal of Experimental Medicine, 2002, vol. 195, pp. 343-351).*
Niedermann et al, Immunity, 1995, vol. 2, pp. 289-299.*
Ashton et al., "GABA-ergic drugs: Exit stage left, enter stage right", Journal of Psychopharmacology, vol. 17, No. 2, pp. 174-178 (2003).
Burch et al., "Priming tissue specific cellular immunity in phase I trial of autologous dendritic cells for prostate cancer", Clinical Cancer Research, vol. 6, pp. 2175-2182 (2000).
Burch et al., "Immunotherapy (APC8015, Provenge®) targeting prostatic acid phosphatase can induce durable remission of meastatic androgen-independent prostate cancer: A phase 2 trial", The Prostate, vol. 60, pp. 197-204 (2004).
Davis et al. "Relationship between the rate of appearance of oxyprenolol in the systematic circulation and the location of an oxyprenolol oros 16/260 drug delivery system within the gastrointestinal tract as determined by scintigraphy", Br. J. Clin. Pharmac., vol. 26, pp. 435-443 (1988).
Dworkin et al., "Advances in neuropathic pain: diagnosis, mechanisms, and treatment recommendations" Archives of Neurology, vol. 60, pp. 1524-1534 (2003).
Fix, "Oral Drug Delivery, Small Intestine and Colon", in *Controlled Delivery*, Mathiowitz, Ed., Wiley & Sons, Inc., pp. 699-700 (1999).
Grundy and Foster, "The nifedipine gastrointestinal therapeutic system (GITS). evaluation of pharmaceutical, pharmacokinetic and pharmacological properties," Clin. Pharmacokinet., vol. 26, pp. 435-443 (1988).
Helguera et al., "Cytokines fused to antibodies and their combinations as therapeutic agents against different peritoneal HER2/neu expressing tumors", Molecular Cancer Therapeutics, vol. 5, No. 4, pp. 1029-1040 (2006).
Hernandez et al., "Novel kidney cancer immunotherapy based on the granulocyte-macrophage colony-stimulating factor and carbonic anhydrase IX fusion gene", Clinical Cancer Research, vol. 9, pp. 1906-1919 (2003).
International Search Report and Written Opinion from PCT Patent Application No. PCT/US2008/003755 mailed Mar. 30, 2008, 16 pages; Application now published as PCT Patent Publication No. WO2008/118369 on Oct. 2, 2008.
Lanier et al., "Immunoreceptor DAP12 bearing a tyrosine-based activation motif is involved in activating NK cells", Nature, vol. 391, pp. 703-707 (1998).
Muscas et al., "Conversion from thrice daily to twice daily administration of gabapentin (GBP) in partial epilepsy: Analysis of clinical efficacy and plasma levels", Seizure, vol. 9, No. 1, pp. 47-50 (2000).
Peng et al., "Expansion and activation of natural killer cells from PBMC for immunotherapy of hepatocellular carcinoma", World J. Gastroenterol., vol. 10, pp. 2119-2123 (2004).

(Continued)

*Primary Examiner* — Karen Canella
(74) *Attorney, Agent, or Firm* — King & Spalding LLP; Peter J. Dehlinger

(57) ABSTRACT

This disclosure relates to methods of inducing a natural killer (NK) cell-mediated immune response and increasing NK activity in a mammal for the treatment of tumors and virus infections, comprising isolating peripheral blood mononuclear cells (PBMCs) from a subject, exposing them in vitro to a protein conjugate comprising granulocyte macrophage colony stimulating factor (GM-CSF) covalently linked to a soluble peptide antigen to activate the PBMCs, and administering the activated PBMCs to the subject. The method also relates to assessing NK cell activity of activated PBMCs to determine whether the subject has had a therapeutically effective response to the protein conjugate.

14 Claims, 5 Drawing Sheets

(56) References Cited

OTHER PUBLICATIONS

Reis et al., "In vivo microbial stimulation induces rapid CD40 ligand-independent production of interleukin 12 by dendritic cells and their redistribution to T cell areas", Journal of Experimental Medicine, vol. 186, No. 11, pp. 1819-1829 (1997).

Rocci et al., "Food-induced gastric retention and absorption of sustained-release procainamide", Clin. Pharmacol. Ther., vol. 42, pp. 45-49 (1987).

Small et al., "Immunotherapy of hormone-refractory prostate cancer with antigen-loaded dendritic cells", Journal of Clinical Oncology, vol. 18, pp. 3894-3903 (2000).

Stevenson et al., "Colonic absorption of antiepileptic agents", Epilepsia, vol. 38, pp. 63-67 (1997).

Vidovic et al., "Antitumor vaccination with HER-2-derived recombinant antigens", Int. J. Cancer, vol. 102, pp. 660-664 (2002).

Welling and Barbhajya, "Influence of food and fluid volume on chlorothiazide bioavailability: Comparison of plasma and urinary excretion methods", J. Pharm. Sci., vol. 71, pp. 32-35 (1982).

Wilding et al., "Relationship between systemic drug absorption and gastrointestinal transit after the simultaneous oral administration of carbamazepine as a controlled-release system and as a suspension of $^{15}$N-labelled drug to healthy volunteers", Br. J. Clin Pharmac., vol. 32, pp. 573-579 (1991).

Williams et al., "Production of recombinant DTctGMCSF fusion toxin in a baculovirus expression vector system for biotherapy of GMCSF-receptor positive hematologic malignancies", Protein Expression and Purification, vol. 13, pp. 210-221 (1998).

\* cited by examiner

METHODS FOR INDUCING A NATURAL KILLER (NK) CELL-MEDIATED IMMUNE RESPONSE AND FOR INCREASING NK CELL ACTIVITY

This patent application is a continuation of U.S. patent application Ser. No. 12/077,823, filed Mar. 21, 2008, now granted as U.S. Pat. No. 8,153,120, which claims priority to U.S. Provisional Patent Application No. 60/896,461 filed on Mar. 22, 2007, which is incorporated herein in its entirety by reference.

REFERENCE TO SEQUENCE LISTING, TABLE OR COMPUTER PROGRAM

A Sequence Listing is being submitted with this application in the form of a text file, created 21 Mar. 2012, and named "576368130US01SeqList.txt" (24,576 bytes), the contents of which are incorporated herein by reference in their entirety.

FIELD OF THE INVENTION

The present invention relates to the fields of biology and immunology. More particularly, it relates to methods for inducing a natural killer (NK) cell-mediated immune response and increasing the NK cell activity of a mammal in order, for example, to treat tumors or viral infections.

BACKGROUND OF THE INVENTION

The immune system is comprised of many different cell types, factors and organs. These include lymphocytes, monocytes and polymorphonuclear leukocytes, numerous soluble chemical mediators (cytokines and growth factors), the thymus, postnatal bone marrow, lymph nodes, liver and spleen. All of these components work together through a complex communication system to fight against microbial invaders such as bacteria, viruses, fungi and parasites, and against newly arising malignant (tumor) cells. NK cells are bone marrow-derived lymphocytes of the innate arm of the immune system. They are phenotypically defined as expressing the low affinity receptor for the Fc protein of IgG (FcRγIIIA, CD16) and CD 56 in the absence of T cell receptor and its associated CD3 complex (Perussia et al., 2005, *Molecular Immunology* 42: 385-395).

NK cells have vital importance as a first line of defense against infection and tumor proliferation while the adaptive immune system is being activated (French et al., 2003, *Current Opinion in Immunology* 15: 45-51). The primary role of NK cells is to eliminate infected or cancerous cells by direct cellular cytotoxicity (Van der Broek et al., 2000, *Eur. J. Immunology* 25: 3514-3516). The recognition mechanism involved does not utilize the major histocompatability class (MHC) I antigen presentation pathway and thus NK cells are neither antigen or MHC restricted and more importantly do not undergo clonal expansion to be effective (Trinchieri, 1989, *Adv. Immunology* 47: 176-187). In addition to their cytotoxic actions, NK cells have the ability to modulate the immune system by the production of plietropic cytokines upon cellular activation.

The activation of NK cells largely depends on NK triggering receptors, NKG2D, CD16 and the recently identified natural cytotoxicity receptors (NCR) (Arnon et al., 2006, *Seminars in Cancer Biology* 16: 348-358), which include three members: NKp46, NKp44 and NKp30 (Moretta et al., 2002, *Scand. J. Immunol.* 55: 229-232, Bottino et al., 2005, *Trends in Immunology* 26: 221-226). The NCR have recently been designated cluster of differentiation notation, with NKp44 designated CD336.

CD336 encodes a 44 kDa surface glycoprotein characterized by a protein backbone of approximately 29 kDa (Vitale et al., 1998, *J. Exp. Med.* 187: 2065-2072). CD336 is not expressed on resting but only on activated NK cells, thus the surface display of CD336 can be used as a surrogate marker of NK activation (Moretta et al., 2001, *Annu. Rev. Immunol.* 19: 197-223). While CD336 is a pertinent marker of cell activation, the hallmark of NK functionality is the ability to lyse target cells, typically NK lytic activity is measured in vitro using a cell line deficient for surface MHC I expression such as the K562 tumor cell line.

The present inventors have identified novel methods for inducing an NK cell-mediated immune response, for increasing the activity of NK cells and for assessing and detecting an NK cell response in connection with the treatment of viruses and tumors.

BRIEF SUMMARY OF THE INVENTION

In a first aspect, this invention provides a method for inducing a cytotoxic NK cell-mediated immune response in a mammalian subject, which comprises the steps of isolating peripheral blood mononuclear cells (PBMCs) from a subject, exposing the PBMCs in vitro to a protein conjugate comprising granulocyte macrophage colony stimulating factor (GM-CSF) covalently linked to a soluble peptide antigen selected from the group consisting of a tumor associated antigen (TAA) and an oncogene product, under conditions effective to activate the PBMCs, wherein the PBMCs are effective in activating NK cells to produce a cytotoxic cellular response that is higher than that produced by the PBMCs which have not been activated by the protein conjugate, and administering the activated PBMCs to the subject.

In another aspect, the invention provides a method for increasing NK cell activity, comprising the steps of isolating peripheral blood mononuclear cells (PBMCs) from a subject, exposing the PBMCs in vitro to a protein conjugate comprising granulocyte macrophage colony stimulating factor (GM-CSF) covalently linked to a soluble peptide antigen selected from the group consisting of a tumor associated antigen (TAA) and an oncogene product, under conditions effective to activate the PBMCs, wherein the PBMCs are effective in activating NK cells.

In yet another aspect, the invention provides an improvement for determining whether the individual subject is a candidate for additional treatment by administration of the activated PBMCs by assessing the response of an individual subject to an anti-cancer therapy comprising the steps of (a) isolating PBMCs from a subject; (b) exposing the PBMCs in vitro to a protein conjugate comprising granulocyte macrophage colony stimulating factor (GM-CSF) covalently linked to a soluble peptide antigen selected from the group consisting of a tumor associated antigen (TAA) and an oncogene product, under conditions effective to activate the PBMCs; (c) administering the activated PBMCs to the subject; (d) repeating step (a) and (b) at least 10 days after previous step (c) has occurred, (e) assessing the NK activity of the activated PBMCs from the second isolation; and (f) if the NK activity has increased significantly over the level of NK activity prior to the first administration, classifying the subject as a good candidate for additional treatment by activated PBMC administration.

In another aspect, the invention provides a method for determining whether a subject has had a therapeutically effective response to administration of activated PBMCs comprising the steps of (a) isolating PBMCs from a subject; (b) exposing the PBMCs in vitro to a protein conjugate comprising granulocyte macrophage colony stimulating factor (GM-CSF) covalently linked to a soluble peptide antigen selected from the group consisting of a tumor associated antigen (TAA) and an oncogene product, under conditions effective to activate the PBMCs; (c) administering the activated PBMCs to the subject; (d) repeating step (a) and (b) at least 10 days after previous step (c) has occurred, (e) assessing the NK activity of the activated PBMCs from the previous isolation; and (f) determining the change in the NK activity over the level of NK activity of the activated PBMCs prior to the first administration.

The methods of the present invention are particularly suited to the treatment of cancers such as, for example, soft tissue sarcomas, lymphomas, and cancers of the brain, esophagus, uterine cervix, bone, lung, endometrium, bladder, breast, larynx, colon/rectum, stomach, ovary, pancreas, adrenal gland and prostate. Exemplified herein are methods for the treatment of prostate and/or breast cancer.

In each of the above aspects of the invention, (i) the PBMCs may be antigen presenting cells (APCs); (ii) PBMCs may be dendritic cells (DCs); (iii) for use in treating a tumor, the soluble peptide antigen may be a TAA, including a tissue-specific tumor antigen; (iv) for use in treating a tumor, the soluble peptide antigen may be an oncogene product; (v) the protein conjugate may further include a linker peptide joining the GM-CSF to the soluble peptide antigen; (vi) for use in treating prostate cancer, the tissue-specific tumor antigen may be prostatic acid phosphatase (PAP) having at least 95% sequence identity to the sequence depicted as SEQ ID NO: 1; (vii) the protein conjugate may be a fusion protein having at least 95% sequence identity with the sequence depicted as SEQ ID NO: 5; (vii) for use in treating breast cancer, the oncogene product may be Her2; (viii) the protein conjugate may comprise a fusion protein having at least 95% sequence identity with the sequence depicted as SEQ ID NO: 7; the mammalian subject is a human; and (ix) the protein conjugate may be produced in a baculovirus expression system.

Also in aspects of the invention involving the steps of (a) isolating PBMCs from a subject; (b) exposing the PBMCs in vitro to a protein conjugate comprising granulocyte macrophage colony stimulating factor (GM-CSF) covalently linked to a soluble peptide antigen selected from the group consisting of a tumor associated antigen (TAA) and an oncogene product, under conditions effective to activate the PBMCs, and (c) administering the activated PBMCs to the subject; the claimed invention may further comprise repeating steps (a), (b) and (c) at least once with each cycle beginning at least ten days after step (c) has occurred; and steps (a) through (c) may be performed a total of three times and wherein fourteen days has elapsed since the previous step (c) has occurred.

BRIEF DESCRIPTION OF THE DRAWINGS

FIG. 1 shows NK cell activity as measured by CD336 surface expression on CD16+ and CD56+ NK cells before and after culture with sipuleucel-T, an investigative immunotherapeutic agent manufactured by Dendreon Corp, Seattle, Wash., at weeks 0, 2 and 4. FIG. 1 shows that CD336 surface expression on both CD16+ and CD56+ cells is enhanced post-culture. Pre- and post culture cells were surface stained for CD16, CD56 and CD336, and 200,000 events were collected on a Becton Dickinson FACSAria flow cytometer. Gated CD16+ and CD56+ cells were then analyzed for CD336 expression and the percent of CD16+ or CD56+ cells that expressed CD336 then calculated.

FIG. 2 shows NK cell activity as measured by CD336 surface expression on CD16+ and CD56+ NK cells from subjects that received a placebo (cells incubated without the GM-CSF fusion protein) in the double-blind, placebo controlled clinical trial for sipuleucel-T. FIG. 2 shows that CD336 surface expression on both CD16+ and CD56+ cells is not enhanced post-culture. Pre- and post culture cells were surface stained for CD16, CD56 and CD336, and 200,000 events were collected on a Becton Dickinson FACSAria flow cytometer. Gated CD16+ and CD56+ cells were then analyzed for CD336 expression and the percent of CD16+ or CD56+ cells that expressed CD336 then calculated.

FIG. 3 shows sipuleucel-T cell lytic activity against the MHC-I deficient cell line K562 at weeks 0, 2 and 4 for several different subjects. FIG. 2 shows that sipuleucel-T cells generated from the week 2 apheresis from seven different subjects that had received the week 0 treatment, possessed cytotoxic activity as gauged by lysis of the K562 tumor cell line. Sipuleucel-T cells were titrated in triplicate at an effector to target ratio starting at 50:1 against a fixed number of K562 target cells. The cells were incubated at 37° C. for 4 hours after which time the medium was tested in a colorimetric assay for the presence of the intracellular enzyme lactate dehydrogenase (LDH). The degree of lytic activity was thus calculated using the following formula:

$$\% \ Cytotxicity = 100 \times \frac{A - B - C}{D - C}$$

Figure 4:
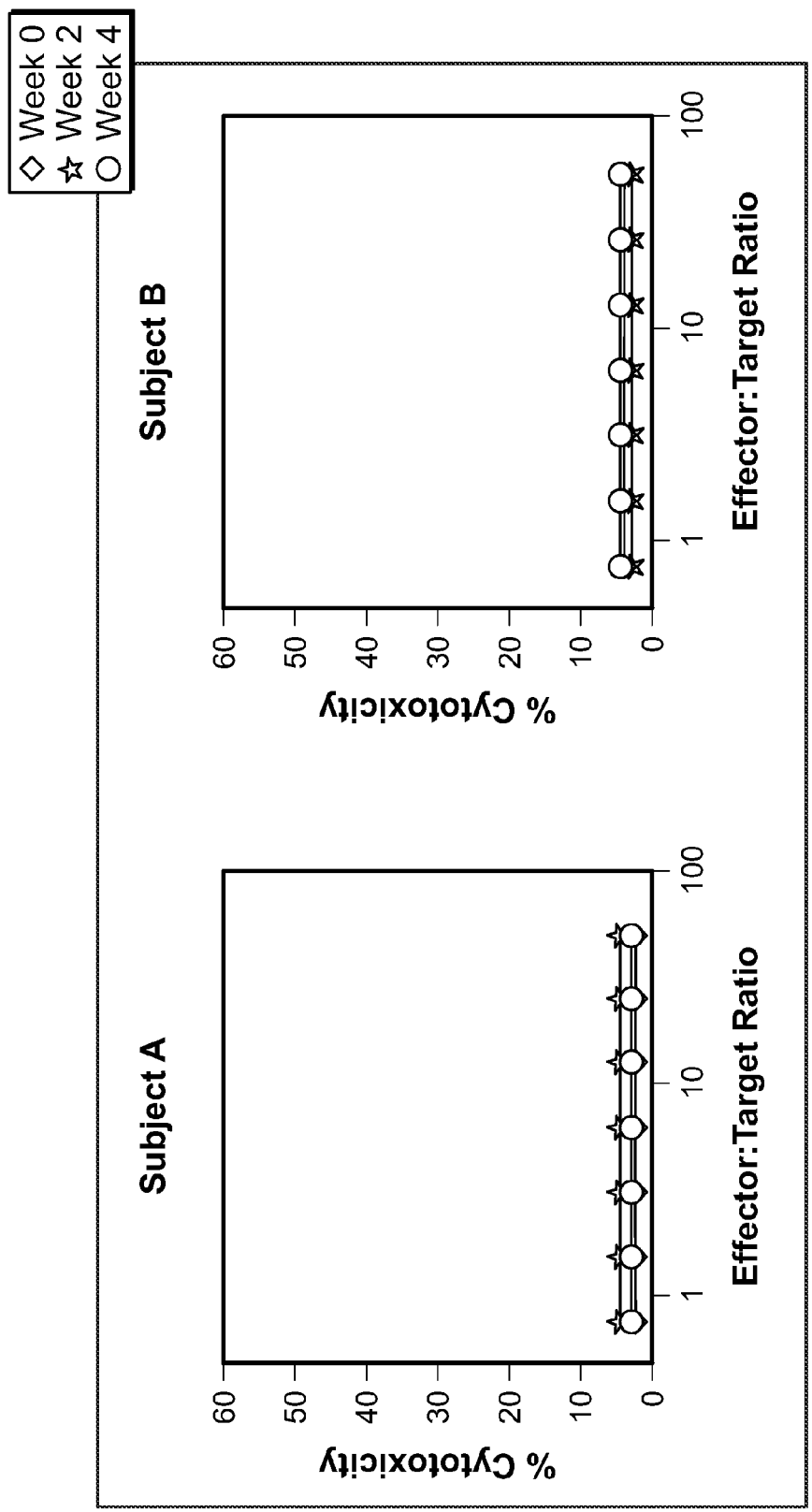

A=LDH from test cell mixture (effector cells+target cells)
B=spontaneous LDH from effector cells
C=spontaneous LDH from target cells
D=maximal LDH from target cells FIG. 4. FIG. 4 shows sipuleucel-T cell lytic activity against the MHC-I deficient cell line K562 at weeks 0, 2 and 4 from two subjects that received a placebo (cells incubated without the GM-CSF fusion protein) in the double bind, placebo cotrolled clinical trial for sipuleucel-T. FIG. 4 shows that cells generated from the week 2 apheresis from two subjects who had received the week 0 placebo, did not possess cytotoxic activity as gauged by lysis of the K562 tumor cell line. Sipuleucel-T cells were titrated in triplicate at an effector to target ratio starting at 50:1 against a fixed number of K562 target cells. The cells were incubated at 37° C. for 4 hours after which time the medium was tested in a colorimetric assay for the presence of the intracellular enzyme lactate dehydrogenase (LDH). The degree of lytic activity was thus calculated using the following formula:

$$\% \ Cytotxicity = 100 \times \frac{A - B - C}{D - C}$$

Figure 5:
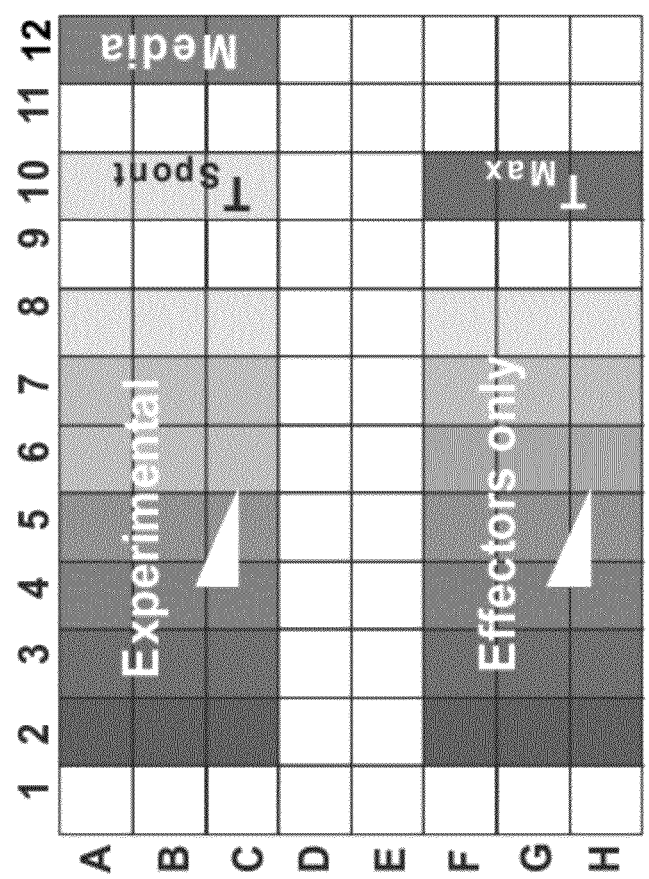

A=LDH from test cell mixture (effector cells+target cells)
B=spontaneous LDH from effector cells
C=spontaneous LDH from target cells
D=maximal LDH from target cells FIG. 5. FIG. 5 is a diagrammatic representation of a portion of a 96 well V-bottomed plate on which the major histocompatability complex (MHC) I negative cell line K562 (also referred to as "target cells") and sipuleucel-T cells (also referred to as "effector cells") were used to assess the NK lytic activity of sipuleucel-T.

SEQ ID NO: 1 is the amino acid sequence of human prostatic acid phosphatase (huPAP) as encoded by the cDNA sequence depicted in SEQ ID NO: 2.

SEQ ID NO: 2 is the nucleotide sequence of a cDNA encoding human prostatic acid phosphatase (huPAP) as depicted in SEQ ID NO: 1.

SEQ ID NO: 3 is the amino acid sequence of a human granulocyte-macrophage colony stimulating factor (huGM-CSF) as encoded by the cDNA sequence depicted in SEQ ID NO: 4.

SEQ ID NO: 4 is the nucleotide sequence of a cDNA encoding human granulocyte-macrophage colony stimulating factor (huGM-CSF) as depicted in SEQ ID NO: 3.

SEQ ID NO: 5 is the amino acid sequence of a human prostatic acid phosphatase/human granulocyte-macrophage colony stimulating factor (huPAP/huGM-CSF) fusion protein as encoded by the cDNA sequence depicted in SEQ ID NO: 6, SEQ ID NO: 6 is the nucleotide sequence of a cDNA encoding human prostatic acid phosphatase/human granulocyte-macrophage colony stimulating factor (huPAP/huGM-CSF) fusion protein as depicted in SEQ ID NO: 5.

SEQ ID NO: 7 is the amino acid sequence of a HER500-human granulocyte-macrophage colony stimulating factor (HER500-huGM-CSF) fusion protein as encoded by the cDNA sequence depicted in SEQ ID NO: 8.

SEQ ID NO: 8 is the nucleotide sequence of a cDNA encoding a HER500-human human granulocyte-macrophage colony stimulating factor (HER500-huGM-CSF) fusion protein as depicted in SEQ ID NO: 7.

DETAILED DESCRIPTION OF THE INVENTION

As described above, the invention provides a method for inducing a cytotoxic NK cell-mediated immune response in a mammalian subject, which comprises the steps of isolating peripheral blood mononuclear cells (PBMCs) from a subject, exposing the PBMCs in vitro to a protein conjugate comprising a GM-CSF having at least 95% sequence identity with the sequence depicted in SEQ ID NO: 3 (GM-CSF), covalently linked to a soluble peptide antigen selected from the group consisting of a tumor associated antigen and an oncogene product, under conditions effective to activate the PBMCs, wherein the PBMCs are effective in activating NK cells to produce a cytotoxic cellular response that is higher than that produced by the PBMCs when not activated by the protein conjugate, and administering the activated PBMCs to the subject.

In another aspect, the invention provides a method for increasing NK cell activity, comprising the steps of isolating peripheral blood mononuclear cells (PBMCs) from a subject, exposing the PBMCs in vitro to a protein conjugate comprising GM-CSF covalently linked to a soluble peptide antigen selected from the group consisting of a tumor associated antigen (TAA) and an oncogene product, under conditions effective to activate the PBMCs, wherein the PBMCs are effective in activating NK cells.

In yet another aspect, the invention provides an improvement for determining whether the individual subject is a candidate for additional treatment by administration of the activated PBMCs by assessing the response of an individual subject to an anti-cancer therapy comprising the steps of (a) isolating PBMCs from a subject; (b) exposing the PBMCs in vitro to a protein conjugate comprising GM-CSF covalently linked to a soluble peptide antigen selected from the group consisting of a tumor associated antigen (TAA) and an oncogene product, under conditions effective to activate the PBMCs; (c) administering the activated PBMCs to the subject; (d) repeating step (a) and (b) at least 10 days after previous step (c) has occurred, (e) assessing the NK activity of the activated PBMCs from the second isolation; and (f) if the NK activity has increased significantly over the level of NK activity prior to the first administration, classifying the subject as a good candidate for additional treatment by activated PBMC administration.

In another aspect, the invention provides a method for determining whether a subject has had a therapeutically effective response to administration of activated PBMCs comprising the steps of (a) isolating PBMCs from a subject; (b) exposing the PBMCs in vitro to a protein conjugate comprising GM-CSF covalently linked to a soluble peptide antigen selected from the group consisting of a tumor associated antigen (TAA) and an oncogene product, under conditions effective to activate the PBMCs; (c) administering the activated PBMCs to the subject; (d) repeating step (a) and (b) at least 10 days after previous step (c) has occurred, (e) assessing the NK activity of the activated PBMCs from the previous isolation; and (f) determining the change in the NK activity over the level of NK activity of the activated PBMCs prior to the first administration.

In each of the aspects of the invention, (i) the PBMCs may be antigen presenting cells (APCs); (ii) PBMCs may be dendritic cells (DCs); (iii) for use in treating a tumor, the soluble peptide antigen may be a TAA, including a tissue-specific tumor antigen; (iv) for use in treating a tumor, the soluble peptide antigen may be an oncogene product; (v) the protein conjugate may further include a linker peptide joining the GM-CSF to the soluble peptide antigen; (vi) for use in treating prostate cancer, the tissue-specific tumor antigen may be prostatic acid phosphatase (PAP) having at least 95% sequence identity to the sequence depicted as SEQ ID NO: 1; (vii) the protein conjugate may be a fusion protein having at least 95% sequence identity with the sequence depicted as SEQ ID NO: 5; (vii) for use in treating breast cancer, the oncogene product may be Her2; (viii) the protein conjugate may comprise a fusion protein having at least 95% sequence identity with the sequence depicted as SEQ ID NO: 7; the mammalian subject is a human; and (ix) the protein conjugate may be produced in a baculovirus expression system.

Immunotherapeutic Compositions

Within certain embodiments, the present invention provides that the PBMCs are isolated antigen presenting cells (APCs) obtained from a subject. In certain embodiments, the APCs are stimulated by exposure in vitro to a tumor-associated antigen (TAA). The tumor-associated antigen may be a tissue-specific tumor antigen. As used herein, The tumor-associated antigen and/or the tissue-specific tumor antigen are a component of an immunotherapeutic composition that comprises a protein conjugate wherein the protein conjugate comprises an N-terminal moiety and a C-terminal moiety, wherein the C-terminal moiety has at least 95% sequence identity with the sequence depicted as SEQ ID NO: 3 (huGM-CSF or GM-CSF). In certain preferred embodiments, the APCs are stimulated with a protein conjugate comprising an N-terminal moiety, having at least 95% sequence identity with the sequence depicted in SEQ ID NO: 1 (huPAP or PAP) or an active fragment, derivative, or variant of huPAP. In an especially preferred embodiment the subject's APCs are stimulated by a protein conjugate comprising the sequence depicted in SEQ ID NO: 5 (PAP/GM-CSF)

In other embodiments, the APCs are stimulated in vitro by exposure to a protein conjugate comprising a C-terminal moiety comprising GM-CSF and an N-terminal moiety comprising an oncogene product. The oncogene product is a component of an immunotherapeutic composition that comprises a protein conjugate wherein the protein conjugate comprises an N-terminal moiety and a C-terminal moiety, wherein the C-terminal moiety is GM-CSF. In a preferred embodiment, the N-terminal moiety having at least 95% sequence identity with the sequence depicted in SEQ ID NO: 7 (HER500-hGM-CSF). The immunotherapeutic compositions described herein are effective in inducing an NK cell-mediated immune response against the protein conjugate. The NK cell-mediated immune response is higher than that produced by APCs when not exposed to the protein conjugate. Specific preferred embodiments provide that the APCs are dendritic cells (DCs).

APCs and DCs

As used herein, the term "antigen presenting cells" or "APCs" refers to cells that are capable of inducing an NK cell-mediated immune response, and include, but are not limited to certain macrophages, B cells, and, most preferable, dendritic cells (DCs). "Dendritic cells" or "DCs" are members of a diverse population of morphologically similar cell types found in lymphoid or non-lymphoid tissues. These cells are characterized by their distinctive morphology and high levels of surface MHC class II expression (Steinman et al., 1991, *Ann. Rev. Immunol.* 9: 271).

APCs and DCs may be isolated from a number of tissue sources, and conveniently from peripheral blood. APCs and DCs may be isolated by routine methodologies that are readily available in the art. An exemplary suitable methodology for isolation of DCs is disclosed in U.S. Pat. Nos. 5,976,546, 6,080,409, and 6,210,662, each of these patents is incorporated herein by reference. Briefly, buffy coat cells may be prepared from peripheral blood. Cells may be harvested from leukopacs, layered over columns of organosilanized colloidal silica (OCS) separation medium (prepared as described by Dorn in U.S. Pat. No. 4,927,749, incorporated herein by reference) at a density 1.0770 g/ml, pH 7.4, 280 mOsm/kg $H_2O$) in centrifuge tubes or devices. The OCS medium is preferable prepared by reacting and thus blocking the silanol groups of colloidal silica (approximately 10-20 nm diameter particles) with an alkyl tri-methoxy silane reagent.

In one embodiment, the OCS density gradient material is diluted to an appropriate specific density in a physiological salt solution supplemented with polyvinylpyrolidone (PVP). The tubes are centrifuged and the PBMCs present at the interface, are harvested.

PBMC are resuspended and centrifuged again to remove platelets and may optionally be spun through columns of OCS (density 1.0650 g/ml, 280 mOsm/kg $H_2O$). The resulting interface and PBMCs are harvested and washed with D-PBS by centrifugation. The pellet fraction is resuspended in cell culture medium and cultured with the protein conjugate in a humidified 5% $CO_2$ incubator for approximately 40 hours. Following incubation, the cells are harvested.

In a preferred embodiment, sipuleucel-T, an investigative immunotherapeutic agent manufactured by Dendreon Corp, (Seattle, Wash.) is generated from a subject's own blood cells using an apheresis. The subject's apheresis cells are centrifuged to remove autologous plasma, they are then resuspended in 0.9% sodium chloride USP solution and passed through a buoyant density solution (BDS) of 1.077 g/ml gravity. The interface cells are collected and washed in 0.9% sodium chloride USP solution after which they are then passed over a BDS 1.065 g/ml gravity separation solution. The cells that pass through the density solution are then collected and washed in 0.9% sodium chloride USP solution. These cells, termed BDS65 cells are cultured in AIM-V® culture medium for up to 44 hours with PA2024, a fusion protein comprising human prostatic acid phosphatase fused to human GM-CSF. The cultured cells are then washed out of the culture medium and resuspended in lactated ringers solution and are re-infused back into the subject. This process is performed three times, with each cycle of apheresis and culture being conducted two weeks apart.

Protein Conjugates

Preferred protein conjugates comprise an N-terminal moiety which includes at least a portion of a tumor associated antigen or an oncogene product and a C-terminal moiety which includes the dendritic cell binding protein, GM-CSF.

As used herein, the term "tumor-associated antigen" refers to an antigen that is characteristic of a tissue type, including specific tumor tissues. An example of a tumor-associated antigen expressed by a tumor tissue is the antigen prostatic acid phosphatase (PAP), which is present on over 90% of all prostate tumors. The term "tissue specific tumor antigen" can be characterized as (i) inclusive of antigens that are common to a specific type of tumor and (ii) exclusive of antigens that are specific only to an individual tumor. The term "oncogene product" refers to any protein encoded by a gene associated with cellular transformation. Examples of oncogene products include, for example, Her2, p21RAS, and p53.

The terms "antigen presenting cell binding protein" and "dendritic cell binding protein" refer to any protein for which receptors are expressed on an APC or a DC, respectively. Examples of antigen presenting cell binding proteins and dendritic cell binding proteins include, but are not limited to, GM-CSF, IL-1, TNF, IL-4, CD40L, CTLA4, CD28, and FLT-3 ligand.

"Protein conjugates," as disclosed herein, refer to covalent complexes formed between the N-terminal moiety and the C-terminal moiety. Protein conjugates between tumor associated antigens/tumor-specific antigens/oncogene products and antigen presenting cell binding proteins/dendritic cell binding proteins may be complexed either chemically or as a fusion protein.

The exemplary PAP/GM-CSF protein conjugate disclosed herein was previously described within U.S. Pat. Nos. 5,976,546, 6,080,409, and 6,210,662, each of which is incorporated herein by reference and is presented herein as SEQ ID NO: 5. This protein conjugate is a fusion protein between a 386 amino acid portion of PAP at the N-terminus and a 127 amino acid portion of GM-CSF at the C-terminus. In addition, the PAP/GM-CSF fusion protein further comprises, between the N-terminal moiety and the C-terminal moiety, a two amino acid peptide linker having the sequence gly-ser. The fusion protein is manufactured in a Baculovirus expression system using sf21 insect cells.

As described above, the PAP/GM-CSF protein conjugate is exposed to a subject's PBMCs under conditions effective to activate the PBMCs and the activated PBMCs are administered to the subject to induce a cytotoxic NK cell-mediated immune response.

The term "administration" or "administering" refers to various methods of contacting a substance with a mammal, especially a human. Modes of administration may include, but are not limited to, methods that involve contacting the substance intravenously, intraperitoneally, intranasally, transdermally, topically, subcutaneously, parentally, intramuscularly, orally, or systemically, and via injection, ingestion, inhalation, implantation, or adsorption by any other means. One exemplary means of administration of the protein conjugates or fusion proteins of this invention is via intravenous delivery, where the protein conjugate or fusion protein can be formulated as an aqueous solution, a suspension, or an emulsion, etc. Other means for delivering the protein conjugates or fusion proteins of this invention includes intradermal injection, subcutaneous injection, intramuscular injection or transdermal application as with a patch.

Another exemplary protein conjugate disclosed herein is the HER500-hGM-CSF fusion protein that was previously described within U.S. Pat. Nos. 5,976,546, 6,080,409, 6,210,662, and 7,060,279 each of which is incorporated herein by reference and is presented herein as SEQ ID NO: 7. This protein conjugate is a fusion protein that is composed of 289 amino acids from the N-terminal extra-cellular domain and 217 amino acids from the C-terminal intra-cellular domain of Her2 fused to 127 amino acids of human GM-CSF at the C-terminus. The fusion protein is manufactured in a Baculovirus expression system using sf21 insect cells.

In a preferred embodiment, the invention provides a method of inducing a cytotoxic NK cell-mediated immune response in a human subject comprising the steps of (a) isolating APCs from the subject; (b) exposing the APCs in vitro to a protein conjugate comprising GM-CSF covalently linked to PAP, under conditions effective to activate APCs; (c) administering the activated APCs to the subject; and (d) repeating steps (a)-(c) at least once with each cycle beginning at least 10 days after step (c) has occurred. In an especially preferred embodiment, steps (a)-(c) are repeated one time with step (a) occurring 14 days after step (c).

In another aspect, the invention provides a method for increasing NK cell activity in a patient, comprising the steps of (a) isolating APCs from the patient; (b) exposing the APCs in vitro to a protein conjugate comprising GM-CSF covalently linked to PAP, under conditions effective to activate APCs; (c) administering the activated APCs to the patient; and (d) repeating steps (a)-(c) at least once with each cycle beginning at least 10 days after step (c) has occurred. In an especially preferred embodiment, steps (a)-(c) are repeated one time with step (a) occurring 14 days after step (c).

In another aspect, the invention provides a method of detecting in a subject a cytotoxic NK cell-mediated immune response comprising the steps of (a) isolating APCs from the subject; (b) exposing the APCs in vitro to a protein conjugate comprising GM-CSF covalently linked to a soluble peptide antigen selected from the group consisting of a tissue-specific tumor antigen and an oncogene product, under conditions effective to activate the APCs; (c) administering the activated APCs to the subject; (d) repeating steps (a) and (b); and (e) detecting an NK cell response in the activated PBMCs. In certain embodiments of the invention, the NK cell response is detected in vitro by CD336 surface expression. In other embodiments of the invention, the NK cell response is detected in vitro by lysis of the K562 tumor line.

Evaluation of NK Cell Activation

Figure 1:
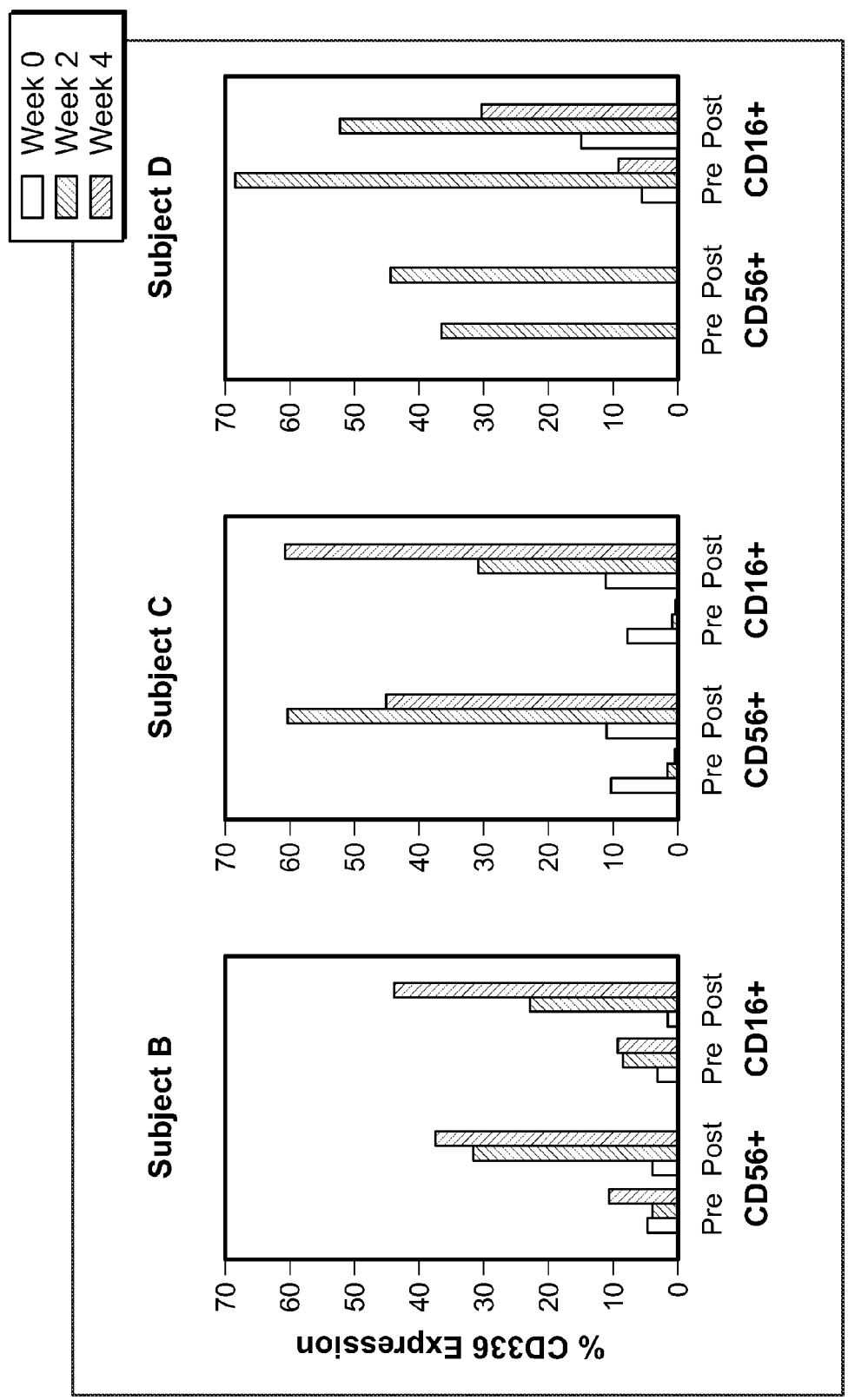
FIG. 1.

In one embodiment of the invention, NK cell activation is evaluated by flow cytometry of CD336 surface expression. APCs are obtained from subjects as described above and evaluated before and after culture with the protein conjugates described above. Pre- and post culture cells were surface stained for CD16, CD56 and CD336, and data were collected on a Becton Dickinson FACSAria flow cytometer. Gated CD16+ and CD56+ cells are then analyzed for CD336 expression and the percent of CD16+ or CD56+ cells that expressed CD336 then calculated. The results, as shown in FIG. 1, show that NK cell activity is enhanced post-culture with a PAP/GM-CSF protein conjugate and subsequent administration to the subject.

Figure 2:
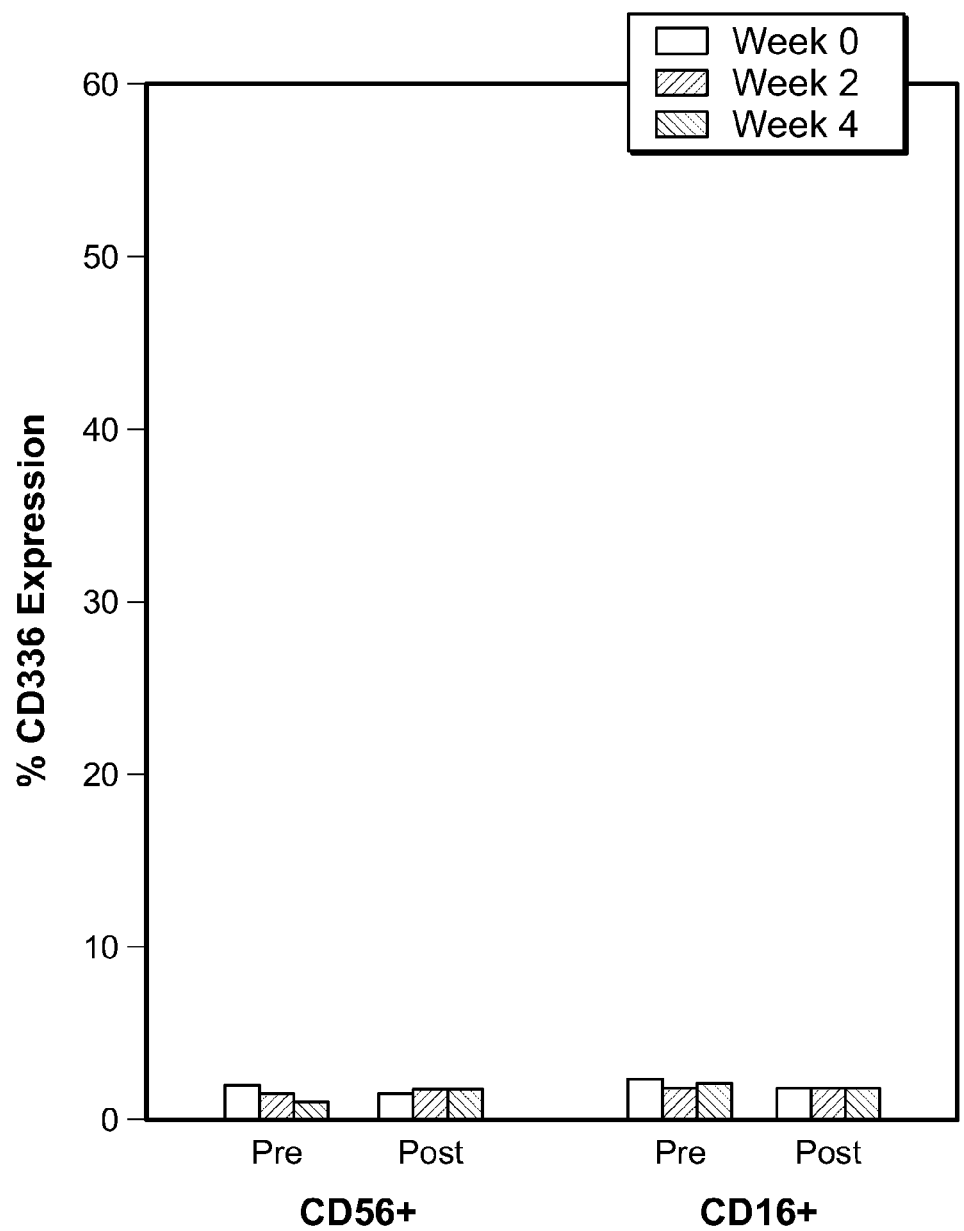
FIG. 2.

In another embodiment of the invention, NK cell activation is evaluated by lysis of the K562 tumor cell line. The K562 cell line is widely used as a target for NK activity as it is MHC class I negative and therefore cannot present either autologous or antigen derived peptides (Ortaldo et al., 1977, *J. Natl. Cancer Inst.* 59: 77-82). The details of material and methods used for the NK lytic cell assay are described below in Example 2. The results, as shown in FIG. 2, show that APCs generated from the week 2 apheresis from subjects undergoing treatment with sipuleucel-T possessed cytotoxic activity as gauged by lysis of the K562 cell line.

EXAMPLES

The following examples are provided by way of illustration only and not by way of limitation. Those of skill in the art will readily recognize a variety of non-critical parameters that could be changed or modified to yield essentially similar results.

Example 1

Materials and Methods

PA2024 is a proprietary recombinant fusion protein containing PAP and GM-CSF sequences manufactured by Dendreon Corporation (Seattle, Wash.) for the investigational cellular immunotherapy sipuleucel-T. PA2024 is expressed in a baculovirus system.

All subject and healthy donor specimens were collected according to investigator sponsored protocols approved by the appropriate Investigational Review Board. After receiving informed consent, white blood cells were collected by apheresis and prepared for transport and/or processing. The subject's apheresis cells were centrifuged to remove autologous plasma, they are then resuspended in 0.9% sodium chloride USP solution and passed through a buoyant density solution (BDS) of 1.077 g/ml gravity. The interface cells were collected and washed in 0.9% sodium chloride USP solution after which they were then passed over a BDS 1.065 g/ml gravity separation solution. The cells that pass through the density solution were then collected and washed in 0.9% sodium chloride USP solution. These cells, termed BDS65 cells were cultured in AIM-V® culture medium for up to 44 hours with PA2024, a fusion protein comprising human prostatic acid phosphatase fused to human GM-CSF. The cultured cells were then washed out of the culture medium and resuspended in lactated ringers solution and were re-infused back into the subject. This process was performed three times, with each cycle of apheresis and culture being conducted two weeks apart.

$1 \times 10^7$ pre-culture and post-culture cells were pelletted by centrifugation and then resuspended in 1 ml of Dulbeccos Phosphate Buffered Saline (D-PBS) containing 10% normal mouse serum (NMS) and incubated at room temperature for 10 minutes. After this time the cells were then centrifuged again and the supernatant was aspirated and the cells were resuspended in 1 ml of staining buffer (D-PBS containing 2% Bovine Serum Albumin—BSA). Aliquots of $1 \times 10^6$ cells were then stained with the following combination of antibodies in the wells of a 96 well round bottom staining plate: Fluoroisothiocyanate (FITC) labeled murine IgG1 together with Phycoerythrin (PE) labeled murine IgG1 and Phycoerythrin-Cyanate 5 (PE-Cy5) labeled murine IgG1, FITC labeled murine anti-human CD16 together with PE labeled murine anti-human CD336 and PE-Cy5 labeled murine anti-human CD56. The cells were incubated in the dark at 4° C. for 20 minutes after which time 100 µl of staining buffer was added and the plate was centrifuged for 5 minutes, the supernatant was aspirated off and the cells were then resuspended in a total volume of 200 µl of D-PBS containing 1% parformaldehyde. Fixed cells were then acquired on a Becton Dickinson FACSAria where a total of 200,000 gated events were collected. Flow data was then analyzed using Beckman Coulter CXP software; the cells stained with FITC labeled murine IgG1, PE labeled murine IgG1 and PECy5 labeled murine IgG1 were used to establish non specific staining. To define the CD16+ and CD56+ NK cell populations, the signals for these surface markers had to be greater than the signal from the FITC or PECy5 labeled murine IgG1 stained cells. Gated CD16+ and CD56+ NK cells were then assessed for CD336 staining, with positive staining for CD336 being a signal that was greater than that detected by staining with PE labeled murine IgG1 and the number of CD16+ or CD56+ cells positive for CD336 were expressed as a percentage of the CD16+ or CD56+ NK cell populations.

Results

The results, as presented in FIG. 1, show that CD336 surface expression on both CD16+ and CD56+ cells is enhanced post-culture with sipuleucel-T. The results, as presented in FIG. 2, also show that CD336 expression is not enhanced for the subjects that did not receive sipuleucel-T.

Example 2

Materials and Methods

PA2024 is a proprietary recombinant fusion protein containing PAP and GM-CSF sequences manufactured by Dendreon Corporation (Seattle, Wash.) for the investigational cellular immunotherapy sipuleucel-T. PA2024 is expressed in a baculovirus system.

All subject and healthy donor specimens were collected according to investigator sponsored protocols approved by the appropriate Investigational Review Board. After receiving informed consent, white blood cells were collected by apheresis and prepared for transport and/or processing. The subject's apheresis cells were centrifuged to remove autologous plasma, they are then resuspended in 0.9% sodium chloride USP solution and passed through a buoyant density solution (BDS) of 1.077 g/ml gravity. The interface cells were collected and washed in 0.9% sodium chloride USP solution after which they were then passed over a BDS 1.065 g/ml gravity separation solution. The cells that pass through the density solution were then collected and washed in 0.9% sodium chloride USP solution. These cells, termed BDS65 cells were cultured in AIM-V® culture medium for up to 44 hours with PA2024, a fusion protein comprising human prostatic acid phosphatase fused to human GM-CSF. The cultured cells were then washed out of the culture medium and resuspended in lactated ringers solution and were re-infused back into the subject. This process was performed three times, with each cycle of apheresis and culture being conducted two weeks apart.

NK lytic activity of sipuleucel-T was determined by assessing the degree of lysis of the major histocompatability complex (MHC) I negative cell line K562, also referred to as target cells, by use of a Non-Radioactive Cytotoxicity Assay (Promega Cat#G1780, Instructions Part #TB163). K562 cells were maintained in log phase culture in standard RPMI1640 media supplemented with 10% Fetal Bovine Serum (FBS) and on the day of use were washed out of the RPMI/10% FBS medium by centrifugation. K562 cells were then resuspended in RPMI1640 medium supplemented with 5% Human Serum (HS) at a concentration of $2.5 \times 10^5$/ml. $15 \times 10^6$ sipuleucel-T cells, also referred to as effector cells, were washed and also resuspended in 600 µl of RPMI/5% HS and 100 µl of the effector cells were dispensed in triplicate into the wells of a 96 well V-bottomed plate, in the first column of the Experimental and Effectors only section of the plate, as detailed in FIG. 5.

The first column of cells represents the highest effector: target ratio, 100 µl of RPMI/5% HS was then dispensed into every triplicate set of wells of the Experimental, Effectors only, $T_{max}$, (Target maximal release), $T_{Spont}$(Target spontaneous release), and media sets. The plate was then centrifuged and the Effector cells were then serially diluted down the Experimental and Effectors only by transferring 100 µl of volume across the plate of the two aforementioned sets. $2.5 \times 10^4$ target cells were then dispensed in triplicate into the wells of the Experimental, $T_{Spont}$ and $T_{Max}$, sets and a further 100 µl of RPMI/5% HS was added to the Media wells. The plate was then incubated for 3.5 hours at 37° C., 5% $CO_2$ after which time 20 µl of 10× lysis buffer was added to the $T_{Max}$ wells and the plate was then incubated for a further 30 minutes. The plate was then centrifuged for 4 minutes at 250G. 50 µl of supernatant was then transferred from each well to a 96 well black walled flat bottomed plate and an equal volume of substrate buffer was added to each well and the plate incubated at room temperature for 30 minutes. After this time 50 µl of stop solution was added and the optical density of each well was determined on an ELISA plate reader at a wavelength of 490 nm. The degree of lytic activity was the calculated using the following formula:

$$\% \text{ Cytotxicity} = \frac{\text{Experimental} - \text{Effector Spontaneous} - \text{Target Spontaneous}}{\text{Target Maximum} - \text{Target Spontaneous}}$$

Results

Figure 3:
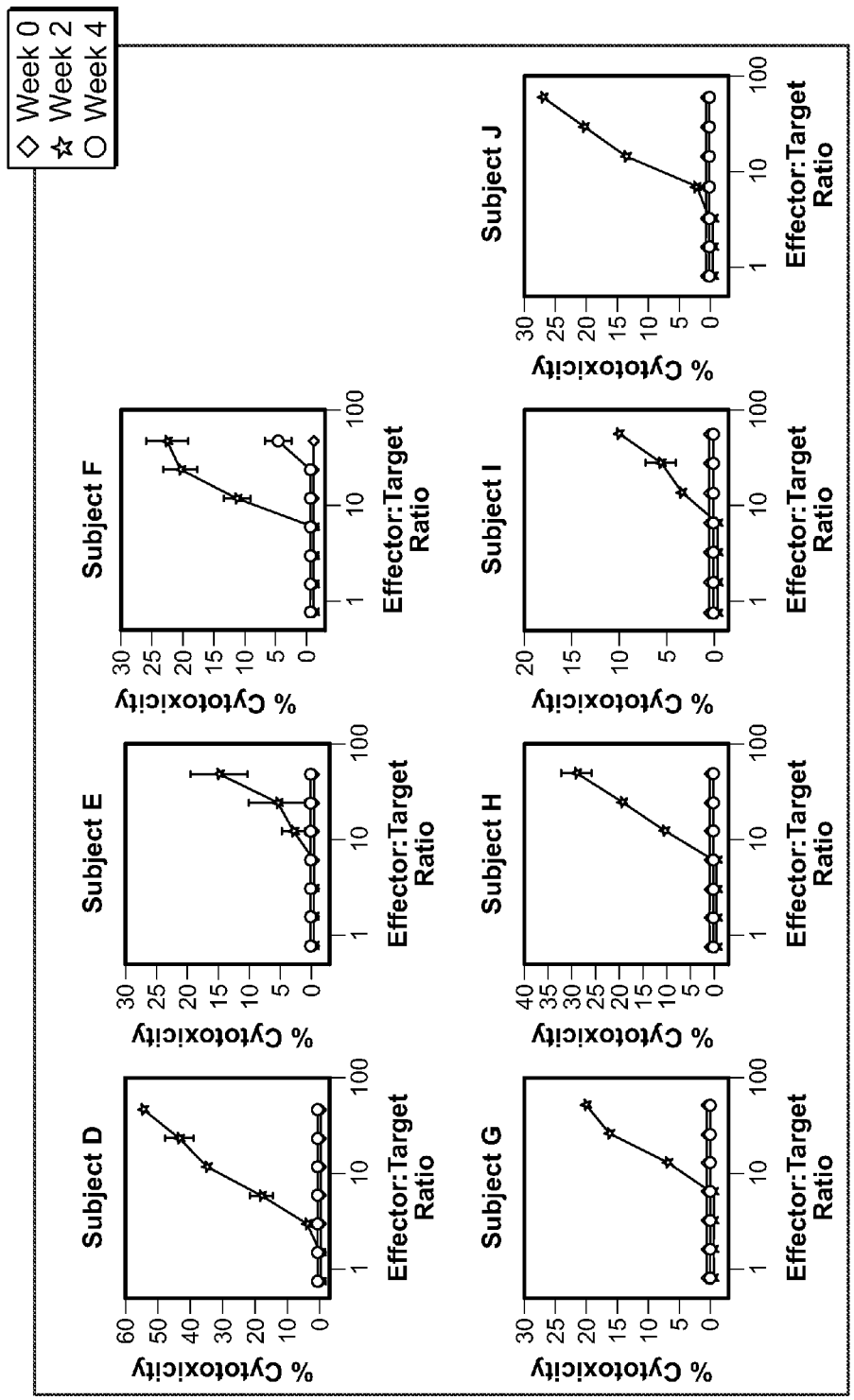
FIG. 3.

The results, as presented in FIG. 3, show that sipuleucel-T cells generated from the week 2 apheresis of treated subjects possessed cytotoxic activity as gauged by lysis of the K562 tumor cell line. The results, as presented in FIG. 4, also show that NK lytic activity is not generated at week 2 in the placebo subjects.

All patents, patent applications, and other publications cited in this application, including published amino acid or polynucleotide sequences, are incorporated by reference in the entirety for all purposes.

What is claimed is:

1. A method for detecting a cytotoxic NK cell-mediated immune response in a subject, comprising:
   (a) isolating peripheral blood mononuclear cells (PBMCs) comprising dendritic cells from the subject;
   (b) exposing said PBMCs in vitro to a protein conjugate comprising granulocyte macrophage colony stimulating factor (GM-CSF) covalently linked to a soluble peptide antigen, said protein conjugate comprising SEQ ID NO: 5 or SEQ ID NO: 7, under conditions effective to activate said PBMCs;
   (c) assessing the level of an NK cell response in the activated PBMCs;
   (d) administering said activated PBMCs to the subject;
   (e) repeating steps (a) and (b) at least 10 days after the previous step (d) has occurred, resulting in a second isolation of PBMCs; and
   (f) assessing the level of an NK cell response in the activated PBMCs from the second isolation,
   wherein said activated PBMCs are effective in activating NK cells to produce a cytotoxic cellular response at a level higher than that produced by the PBMCs which have not been activated by the protein conjugate.

2. The method of claim 1, wherein said protein conjugate comprises a fusion protein having the sequence depicted as SEQ ID NO: 5.

3. The method of claim 1, wherein said protein conjugate comprises a fusion protein having the sequence depicted as SEQ ID NO: 7.

4. The method of claim 1, wherein said mammalian subject is a human.

5. The method of claim 1, wherein said protein conjugate is produced in a baculovirus expression system.

6. The method of claim 1, wherein said method further comprises repeating steps (a), (b) and (c) at least once with each cycle beginning at least 14 days after step (c) has occurred.

7. The method of claim 6, wherein said step (d) is performed in vitro by CD336 surface expression.

8. The method of claim 6, wherein said step (d) is performed in vitro lysis of the K562 tumor line.

9. A method for determining whether a subject has had a therapeutically effective response to a protein conjugate, comprising,
   (a) isolating PBMCs comprising dendritic cells from the subject;
   (b) exposing said PBMCs in vitro to a protein conjugate comprising granulocyte macrophage colony stimulating factor (GM-CSF) covalently linked to a soluble peptide antigen, said protein conjugate comprising SEQ ID NO: 5 or SEQ ID NO: 7, under conditions effective to activate said PBMCs;
   (c) administering said activated PBMCs to the subject;
   (d) repeating steps (a) and (b) at least 10 days after step (c) has occurred; and
   (e) determining a change in NK cell activity of the activated PBMCs.

10. The method of claim 9, wherein determining step (e) includes assessing the NK activity of the activated PBMCs from the previous isolation; and determining the change in the NK activity over the level of NK activity of the activated PBMCs prior to the first administration.

11. The method of claim 9, wherein said step (e) is performed in vitro by CD336 surface expression.

12. The method of claim 9, wherein said step (e) is performed in vitro lysis of the K562 tumor line.

13. The method of claim 12, wherein said steps (a) through (c) are performed a total of two times and wherein 14 days has elapsed since the previous step (c) has occurred.

14. The method of claim 9, wherein said steps (a) through (c) are performed a total of three times and wherein 14 days has elapsed since the previous step (c) has occurred.

* * * * *

SEQUENCE LISTING

<160> NUMBER OF SEQ ID NOS: 8

<210> SEQ ID NO 1
<211> LENGTH: 386
<212> TYPE: PRT
<213> ORGANISM: Homo sapiens

<400> SEQUENCE: 1

Met Arg Ala Ala Pro Leu Leu Ala Arg Ala Ala Ser Leu Ser Leu
 1               5                  10                  15

Gly Phe Leu Phe Leu Leu Phe Phe Trp Leu Asp Arg Ser Val Leu Ala
            20                  25                  30

Lys Glu Leu Lys Phe Val Thr Leu Val Phe Arg His Gly Asp Arg Ser
        35                  40                  45

Pro Ile Asp Thr Phe Pro Thr Asp Pro Ile Lys Glu Ser Ser Trp Pro
    50                  55                  60

Gln Gly Phe Gly Gln Leu Thr Gln Leu Gly Met Glu Gln His Tyr Glu
65                  70                  75                  80

Leu Gly Glu Tyr Ile Arg Lys Arg Tyr Arg Lys Phe Leu Asn Glu Ser
                85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
    130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
        195                 200                 205

Val Tyr Asp Pro Leu Tyr Cys Glu Ser Val His Asn Phe Thr Leu Pro
    210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Ser Gly Leu Gln Met Ala Leu Asp Val Tyr Asn
    290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365

Ser Thr Glu Cys Met Thr Thr Asn Ser His Gln Gly Thr Glu Asp Ser
        370                 375                 380

Thr Asp
385

<210> SEQ ID NO 2
<211> LENGTH: 3089
<212> TYPE: DNA
<213> ORGANISM: Homo sapiens

<400> SEQUENCE: 2

| | | | | | |
|---|---|---|---|---|---|
| agcagttcct | cctaactcct | gccagaaaca | gctctcctca | acatgagagc | tgcacccctc | 60 |
| ctcctggcca | gggcagcaag | ccttagcctt | ggcttcttgt | ttctgctttt | tttctggcta | 120 |
| gaccgaagtg | tactagccaa | ggagttgaag | tttgtgactt | tggtgtttcg | gcatggagac | 180 |
| cgaagtccca | ttgacacctt | tcccactgac | cccataaagg | aatcctcatg | gccacaagga | 240 |
| tttggccaac | tcacccagct | gggcatggag | cagcattatg | aacttggaga | gtatataaga | 300 |
| aagagatata | gaaaattctt | gaatgagtcc | tataaacatg | aacaggttta | tattcgaagc | 360 |
| acagacgttg | accggacttt | gatgagtgct | atgacaaacc | tggcagccct | gtttccccca | 420 |
| gaaggtgtca | gcatctggaa | tcctatccta | ctctggcagc | ccatcccggt | gcacacagtt | 480 |
| cctctttctg | aagatcagtt | gctatacctg | cctttcagga | actgccctcg | ttttcaagaa | 540 |
| cttgagagtg | agactttgaa | atcagaggaa | ttccagaaga | ggctgcaccc | ttataaggat | 600 |
| tttatagcta | ccttgggaaa | actttcagga | ttacatggcc | aggaccttt  | tggaatttgg | 660 |
| agtaaagtct | acgacccttt | atattgtgag | agtgttcaca | atttcacttt | accctcctgg | 720 |
| gccactgagg | acaccatgac | taagttgaga | gaattgtcag | aattgtccct | cctgtccctc | 780 |
| tatggaattc | acaagcagaa | agagaaatct | aggctccaag | ggggtgtcct | ggtcaatgaa | 840 |
| atcctcaatc | acatgaagag | agcaactcag | ataccaagct | acaaaaaact | tatcatgtat | 900 |
| tctgcgcatg | acactactgt | gagtggccta | cagatggcgc | tagatgttta | caacggactc | 960 |
| cttcctccct | atgcttcttg | ccacttgacg | gaattgtact | ttgagaaggg | ggagtacttt | 1020 |
| gtggagatgt | actaccggaa | tgagacgcag | cacgagccgt | atcccctcat | gctacctggc | 1080 |
| tgcagcccca | gctgtcctct | ggagaggttt | gctgagctgg | ttggccctgt | gatccctcaa | 1140 |
| gactggtcca | cggagtgtat | gaccacaaac | agccatcaag | gtactgagga | cagtacagat | 1200 |
| tagtgtgcac | agagatctct | gtagaaagag | tagctgccct | ttctcagggc | agatgatgct | 1260 |
| ttgagaacat | actttggcca | ttacccccca | gctttgagga | aaatgggctt | tggatgatta | 1320 |
| ttttatgttt | tagggacccc | caacctcagg | caattcctac | ctcttcacct | gaccctgccc | 1380 |
| ccacttgcca | taaaacttag | ctaagttttg | ttttgttttt | cagcgttaat | gtaaagggc  | 1440 |
| agcagtgcca | aaatataatc | agagataaag | cttaggtcaa | agttcataga | gttcccatga | 1500 |
| actatatgac | tggccacaca | ggatcttttg | tatttaagga | ttctyagatt | ttgcttgagc | 1560 |
| aggattagat | aagtctgttc | tttaaatttc | tgaaatggaa | cagatttcaa | aaaaaattcc | 1620 |
| cacaatctag | ggtgggaaca | aggaaggaaa | gatgtgaata | ggctgatggg | gaaaaaacca | 1680 |
| atttacccat | cagttccagc | cttctctcaa | ggagaggcaa | agaaaggaga | tacagtggag | 1740 |
| acatctggaa | agttttctcc | actggaaaac | tgctactatc | tgttttata  | ttctgttaa  | 1800 |
| aatatatgag | gctacagaac | taaaattaa  | aacctctttg | tgtcccttgg | tcctggaaca | 1860 |
| tttatgttcc | ttttaaagaa | acaaaaatca | aactttacag | aaagatttga | tgtatgtaat | 1920 |
| acatatagca | gctcttgaag | tatatatatc | atagcaaata | agtcatctga | tgagaacaag | 1980 |

-continued

```
ctatttgggc acaacacatc aggaaagaga gcaccacgtg atggagtttc tccagaagct    2040
ccagtgataa gagatgttga ctctaaagtt gatttaaggc caggcatggt ggtttacgcc    2100
tataatccca gcattttggg actccgaggt gggcagatca cttgagctca ggagctcaag    2160
atcagcctgg gcaacatggt gaaaccttgt ctctacataa aatacaaaaa cttagatggg    2220
catggtgctg tgtgcctata gtccactact tgtggggcta aggcaggagg atcacttgag    2280
ccccggaggt cgaggctaca gtgacccaag agtgcactac tgtactccag ccagggcaag    2340
agagcgagac cctgtctcaa taaataaata aataaataaa taaataaata aataaaaaca    2400
aagttgatta agaaaggaag tataggccag gcacagtggc tcacacctgt aatccttgca    2460
ttttggaagg ctgaggcagg aggatcactt taggcctggt gtgttcaaga ccagcctggt    2520
caacatagtg agacactgtc tctaccaaaa aaaggaagga agggacacat atcaaactga    2580
aacaaaatta gaaatgtaat tatgttatgt tctaagtgcc tccaagttca aaacttattg    2640
gaatgttgag agtgtggtta cgaaatacgt taggaggaca aaaggaatgt gtaagtctt    2700 aatgccgata tcttcagaaa acctaagcaa acttacaggt cctgctgaaa ctgcccactc    2760
tgcaagaaga aatcatgata tagctttcca tgtggcagat ctacatgtct agagaacact    2820
gtgctctatt accattatgg ataaagatga gatggtttct agagatggtt tctactggct    2880
gccagaatct agagcaaagc catccccct cctggttggt cacagaatga ctgacaaaga    2940
catcgattga tatgcttctt tgtgttattt ccctcccaag taaatgtttg tccttgggtc    3000
cattttctat gcttgtaact gtcttctagc agtgagccaa atgtaaaata gtgaataaag    3060
tcattattag gaagttcaaa aaaaaaaaa                                      3089
```

<210> SEQ ID NO 3
<211> LENGTH: 144
<212> TYPE: PRT
<213> ORGANISM: Artificial Sequence
<220> FEATURE:
<223> OTHER INFORMATION: Synthetic polypeptide construct

<400> SEQUENCE: 3

```
Met Trp Leu Gln Ser Leu Leu Leu Leu Gly Thr Val Ala Cys Ser Ile
 1               5                  10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```

<210> SEQ ID NO 4
<211> LENGTH: 767
<212> TYPE: DNA

-continued

<213> ORGANISM: Artificial Sequence
<220> FEATURE:
<223> OTHER INFORMATION: Synthetic nucleic acid construct

<400> SEQUENCE: 4

```
cggaggatgt ggctgcagag cctgctgctc ttgggcactg tggcctgcag catctctgca      60
cccgcccgct cgcccagccc cagcacgcag ccctgggagc atgtgaatgc catccaggag     120
gcccggcgtc tcctgaacct gagtagagac actgctgctg atgaatgaa acagtagaa      180
gtcatctcag aaatgtttga cctccaggag ccgacctgcc tacagacccg cctggagctg     240
tacaagcagg gcctgcgggg cagcctcacc aagctcaagg ccccttgac catgatagcc      300
agccactaca agcagcactg ccctccaacc ccggaaactt cctgtgcaac ccagattatc     360
acctttgaaa gtttcaaaga gaacctgaag gactttctgc ttgtcatccc ctttgactgc     420
tgggagccag tccaggagtg agaccggcca gatgaggctg gccaagccgg ggagctgctc     480
tctcatgaaa caagagctag aaactcagga tggtcatctt ggagggacca aggggtgggc      540
cacagccatg gtgggagtgg cctggacctg ccctgggcca cactgaccct gatacaggca     600
tggcagaaga atgggaatat ttatactga cagaaatcag taatatttat atatttatat      660
ttttaaaata tttatttatt tatttattta agttcatatt ccatatttat tcaagatgtt     720
ttaccgtaat aattattatt aaaaatatgc ttctaaaaaa aaaaaaa                   767
```

<210> SEQ ID NO 5
<211> LENGTH: 515
<212> TYPE: PRT
<213> ORGANISM: Homo sapiens
<220> FEATURE:
<223> OTHER INFORMATION: Prostatic acid phosphatase-GM-CSF fusion protein

<400> SEQUENCE: 5

```
Met Arg Ala Ala Pro Leu Leu Leu Ala Arg Ala Ala Ser Leu Ser Leu
  1               5                  10                  15

Gly Phe Leu Phe Leu Leu Phe Phe Trp Leu Asp Arg Ser Val Leu Ala
             20                  25                  30

Lys Glu Leu Lys Phe Val Thr Leu Val Phe Arg His Gly Asp Arg Ser
         35                  40                  45

Pro Ile Asp Thr Phe Pro Thr Asp Pro Ile Lys Glu Ser Ser Trp Pro
     50                  55                  60

Gln Gly Phe Gly Gln Leu Thr Gln Leu Gly Met Glu Gln His Tyr Glu
 65                  70                  75                  80

Leu Gly Glu Tyr Ile Arg Lys Arg Tyr Arg Lys Phe Leu Asn Glu Ser
                 85                  90                  95

Tyr Lys His Glu Gln Val Tyr Ile Arg Ser Thr Asp Val Asp Arg Thr
            100                 105                 110

Leu Met Ser Ala Met Thr Asn Leu Ala Ala Leu Phe Pro Pro Glu Gly
        115                 120                 125

Val Ser Ile Trp Asn Pro Ile Leu Leu Trp Gln Pro Ile Pro Val His
    130                 135                 140

Thr Val Pro Leu Ser Glu Asp Gln Leu Leu Tyr Leu Pro Phe Arg Asn
145                 150                 155                 160

Cys Pro Arg Phe Gln Glu Leu Glu Ser Glu Thr Leu Lys Ser Glu Glu
                165                 170                 175

Phe Gln Lys Arg Leu His Pro Tyr Lys Asp Phe Ile Ala Thr Leu Gly
            180                 185                 190

Lys Leu Ser Gly Leu His Gly Gln Asp Leu Phe Gly Ile Trp Ser Lys
```

195                 200                 205
Val Tyr Asp Pro Leu Tyr Cys Gly Ser Val His Asn Phe Thr Leu Pro
210                 215                 220

Ser Trp Ala Thr Glu Asp Thr Met Thr Lys Leu Arg Glu Leu Ser Glu
225                 230                 235                 240

Leu Ser Leu Leu Ser Leu Tyr Gly Ile His Lys Gln Lys Glu Lys Ser
                245                 250                 255

Arg Leu Gln Gly Gly Val Leu Val Asn Glu Ile Leu Asn His Met Lys
            260                 265                 270

Arg Ala Thr Gln Ile Pro Ser Tyr Lys Lys Leu Ile Met Tyr Ser Ala
        275                 280                 285

His Asp Thr Thr Val Ser Gly Leu Gln Met Ala Leu Asp Val Tyr Asn
    290                 295                 300

Gly Leu Leu Pro Pro Tyr Ala Ser Cys His Leu Thr Glu Leu Tyr Phe
305                 310                 315                 320

Glu Lys Gly Glu Tyr Phe Val Glu Met Tyr Tyr Arg Asn Glu Thr Gln
                325                 330                 335

His Glu Pro Tyr Pro Leu Met Leu Pro Gly Cys Ser Pro Ser Cys Pro
            340                 345                 350

Leu Glu Arg Phe Ala Glu Leu Val Gly Pro Val Ile Pro Gln Asp Trp
        355                 360                 365

Ser Thr Glu Cys Met Thr Thr Asn Ser His Gln Gly Thr Glu Asp Ser
    370                 375                 380

Thr Asp Gly Ser Ala Pro Ala Arg Ser Pro Ser Pro Ser Thr Gln Pro
385                 390                 395                 400

Trp Glu His Val Asn Ala Ile Gln Glu Ala Arg Arg Leu Leu Asn Leu
                405                 410                 415

Ser Arg Asp Thr Ala Ala Glu Met Asn Glu Thr Val Glu Val Ile Ser
            420                 425                 430

Glu Met Phe Asp Leu Gln Glu Pro Thr Cys Leu Gln Thr Arg Leu Glu
        435                 440                 445

Leu Tyr Lys Gln Gly Leu Arg Gly Ser Leu Thr Lys Leu Lys Gly Pro
    450                 455                 460

Leu Thr Met Met Ala Ser His Tyr Lys Gln His Cys Pro Pro Thr Pro
465                 470                 475                 480

Glu Thr Ser Cys Ala Thr Gln Ile Ile Thr Phe Glu Ser Phe Lys Glu
                485                 490                 495

Asn Leu Lys Asp Phe Leu Leu Val Ile Pro Phe Asp Cys Trp Glu Pro
            500                 505                 510

Val Gln Glu
        515

<210> SEQ ID NO 6
<211> LENGTH: 1588
<212> TYPE: DNA
<213> ORGANISM: Homo sapiens
<220> FEATURE:
<223> OTHER INFORMATION: Prostatic acid phosphatase-GM-CSF fusion gene

<400> SEQUENCE: 6
cggctctcct caacatgaga gctgcacccc tcctcctggc cagggcagca agccttagcc     60
ttggcttctt gtttctgctt ttttttctggc tagaccgaag tgtactagcc aaggagttga   120
agtttgtgac tttggtgttt cggcatggag accgaagtcc cattgacacc tttcccactg   180
accccataaa ggaatcctca tggccacaag gatttggcca actcacccag ctgggcatgg   240

```
agcagcatta tgaacttgga gagtatataa gaaagagata tagaaaattc ttgaatgagt    300
cctataaaca tgaacaggtt tatattcgaa gcacagacgt tgaccggact ttgatgagtg    360
ctatgacaaa cctggcagcc ctgttttccc cagaaggtgt cagcatctgg aatcctatcc    420
tactctggca gcccatcccg gtgcacacag ttcctctttc tgaagatcag ttgctatacc    480
tgcctttcag gaactgccct cgttttcaag aacttgagag tgagactttg aaatcagagg    540
aattccagaa gaggctgcac ccttataagg atttttatagc taccttggga aaactttcag    600
gattacatgg ccaggacctt tttggaattt ggagtaaagt ctacgaccct ttatattgtg    660
agagtgttca caatttcact ttaccctcct gggccactga ggacaccatg actaagttga    720
gagaattgtc agaattgtcc ctcctgtccc tctatggaat tcacaagcag aaagagaaat    780
ctaggctcca aggggtgtc ctggtcaatg aaatcctcaa tcacatgaag agagcaactc    840
agataccaag ctacaaaaaa cttatcatgt attctgcgca tgacactact gtgagtggcc    900
tacagatggc gctagatgtt tacaacggac tccttcctcc ctatgcttct tgccacttga    960
cggaattgta ctttgagaag ggggagtact ttgtggagat gtactatcgg aatgagacgc   1020
agcacgagcc gtatcccctc atgctacctg gctgcagccc tagctgtcct ctggagaggt   1080
ttgctgagct ggttggccct gtgatccctc aagactggtc cacggagtgt atgaccacaa   1140
acagccatca aggtactgag gacagtacag atggatccgc accgcccgc tcgcccagcc   1200
ccagcacaca gccctgggag catgtgaatg ccatccagga ggcccggcgt ctcctgaacc   1260
tgagtagaga cactgctgct gagatgaatg aaacagtaga agtcatctca gaaatgtttg   1320
acctccagga gccgacctgc ctacagaccc gcctggagct gtacaagcag ggcctgcggg   1380
gcagcctcac caagctcaag ggccccttga ccatgatggc cagccactac aaacagcact   1440
gccctccaac cccggaaact tcctgtgcaa cccagattat cacctttgaa agtttcaaag   1500
agaacctgaa ggactttctg cttgtcatcc cctttgactg ctgggagcca gtccaggagt   1560
gagaccggcc agatgaggct ggccaagc                                       1588
```

<210> SEQ ID NO 7
<211> LENGTH: 690
<212> TYPE: PRT
<213> ORGANISM: Artificial Sequence
<220> FEATURE:
<223> OTHER INFORMATION: HER500-hGM-CSF construct

<400> SEQUENCE: 7

```
Met Arg Ala Ala Pro Leu Leu Leu Ala Arg Ala Ser Leu Ser Leu
 1               5                  10                  15

Gly Phe Leu Phe Leu Leu Phe Phe Trp Leu Asp Arg Ser Val Leu Ala
            20                  25                  30

Lys Glu Leu Ala Arg Gly Ala Ala Ser Thr Gln Val Cys Thr Gly Thr
        35                  40                  45

Asp Met Lys Leu Arg Leu Pro Ala Ser Pro Glu Thr His Leu Asp Met
    50                  55                  60

Leu Arg His Leu Tyr Gln Gly Cys Gln Val Val Gln Gly Asn Leu Glu
65                  70                  75                  80

Leu Thr Tyr Leu Pro Thr Asn Ala Ser Leu Ser Phe Leu Gln Asp Ile
                85                  90                  95

Gln Glu Val Gln Gly Tyr Val Leu Ile Ala His Asn Gln Val Arg Gln
            100                 105                 110

Val Pro Leu Gln Arg Leu Arg Ile Val Arg Gly Thr Gln Leu Phe Glu
        115                 120                 125
```

-continued

```
Asp Asn Tyr Ala Leu Ala Val Leu Asp Asn Gly Asp Pro Leu Asn Asn
130                 135                 140

Thr Thr Pro Val Thr Gly Ala Ser Pro Gly Gly Leu Arg Glu Leu Gln
145                 150                 155                 160

Leu Arg Ser Leu Thr Glu Ile Leu Lys Gly Gly Val Leu Ile Gln Arg
                165                 170                 175

Asn Pro Gln Leu Cys Tyr Gln Asp Thr Ile Leu Trp Lys Asp Ile Phe
                180                 185                 190

His Lys Asn Asn Gln Leu Ala Leu Thr Leu Ile Asp Thr Asn Arg Ser
            195                 200                 205

Arg Ala Cys His Pro Cys Ser Pro Met Cys Lys Gly Ser Arg Cys Trp
210                 215                 220

Gly Glu Ser Ser Glu Asp Cys Gln Ser Leu Thr Arg Thr Val Cys Ala
225                 230                 235                 240

Gly Gly Cys Ala Arg Cys Lys Gly Pro Leu Pro Thr Asp Cys Cys His
                245                 250                 255

Glu Gln Cys Ala Ala Gly Cys Thr Gly Pro Lys His Ser Asp Cys Leu
                260                 265                 270

Ala Cys Leu His Phe Asn His Ser Gly Ile Cys Glu Leu His Cys Pro
            275                 280                 285

Ala Leu Val Thr Tyr Asn Thr Asp Thr Phe Glu Ser Met Pro Asn Pro
290                 295                 300

Glu Gly Arg Tyr Thr Phe Gly Ala Ser Cys Val Thr Ala Cys Pro Tyr
305                 310                 315                 320

Asn Tyr Leu Ser Thr Asp Val Gly Ser Gly Ala Gly Gly Met Val His
                325                 330                 335

His Arg His Arg Ser Ser Ser Thr Arg Ser Gly Gly Gly Asp Leu Thr
            340                 345                 350

Leu Gly Leu Glu Pro Ser Glu Glu Ala Pro Arg Ser Pro Leu Ala
            355                 360                 365

Pro Ser Glu Gly Ala Gly Ser Asp Val Phe Asp Gly Asp Leu Gly Met
370                 375                 380

Gly Ala Ala Lys Gly Leu Gln Ser Leu Pro Thr His Asp Pro Ser Pro
385                 390                 395                 400

Leu Gln Arg Tyr Ser Glu Asp Pro Thr Val Pro Leu Pro Ser Glu Thr
                405                 410                 415

Asp Gly Tyr Val Ala Pro Leu Thr Cys Ser Pro Gln Pro Glu Tyr Val
                420                 425                 430

Asn Gln Pro Asp Val Arg Pro Gln Pro Pro Ser Pro Arg Glu Gly Pro
            435                 440                 445

Leu Pro Ala Ala Arg Pro Ala Gly Ala Thr Leu Glu Arg Ala Lys Thr
450                 455                 460

Leu Ser Pro Gly Lys Asn Gly Val Val Lys Asp Val Phe Ala Phe Gly
465                 470                 475                 480

Gly Ala Val Glu Asn Pro Glu Tyr Leu Thr Pro Gln Gly Gly Ala Ala
                485                 490                 495

Pro Gln Pro His Pro Pro Ala Phe Ser Pro Ala Phe Asp Asn Leu
                500                 505                 510

Tyr Tyr Trp Asp Gln Asp Pro Pro Glu Arg Gly Ala Pro Pro Ser Thr
            515                 520                 525

Phe Lys Gly Thr Pro Thr Ala Glu Asn Pro Glu Tyr Leu Gly Leu Asp
530                 535                 540

Val Pro Ala Ala Ala Pro Ala Arg Ser Pro Ser Pro Ser Thr Gln Pro
545                 550                 555                 560
```

Trp Glu His Val Asn Ala Ile Gln Glu Ala Arg Arg Leu Leu Asn Leu
              565                 570                 575

Ser Arg Asp Thr Ala Ala Glu Met Asn Glu Thr Val Glu Val Ile Ser
          580                 585                 590

Glu Met Phe Asp Leu Gln Glu Pro Thr Cys Leu Gln Thr Arg Leu Glu
      595                 600                 605

Leu Tyr Lys Gln Gly Leu Arg Gly Ser Leu Thr Lys Leu Lys Gly Pro
  610                 615                 620

Leu Thr Met Met Ala Ser His Tyr Lys Gln His Cys Pro Pro Thr Pro
625                 630                 635                 640

Glu Thr Ser Cys Ala Thr Gln Ile Ile Thr Phe Glu Ser Phe Lys Glu
              645                 650                 655

Asn Leu Lys Asp Phe Leu Leu Val Ile Pro Phe Asp Cys Trp Glu Pro
          660                 665                 670

Val Gln Glu Gly Ala Pro Pro Pro Ala Ala Ala His His His His
      675                 680                 685

His His
   690

<210> SEQ ID NO 8
<211> LENGTH: 2070
<212> TYPE: DNA
<213> ORGANISM: Artificial Sequence
<220> FEATURE:
<223> OTHER INFORMATION: HER500-hGM-CSF construct

<400> SEQUENCE: 8
atgagagctg cacccctcct cctggccagg gcagcaagcc ttagccttgg cttcttgttt      60 ctgcttttt tctggctaga ccgaagtgta ctagccaagg agttggcgcg cggggccgcg     120
tcgacccaag tgtgcaccgg cacagacatg aagctgcggc tccctgccag tcccgagacc     180
cacctggaca tgctccgcca cctctaccag ggctgccagg tggtgcaggg aaacctggaa     240
ctcacctacc tgcccaccaa tgccagcctg tccttcctgc aggatatcca ggaggtgcag     300
ggctacgtgc tcatcgctca caaccaagtg aggcaggtcc cactgcagag gctgcggatt     360
gtgcgaggca cccagctctt tgaggacaac tatgccctgg ccgtgctaga caatggagac     420
ccgctgaaca taccaccccc tgtcacaggg gcctccccag gaggcctgcg ggagctgcag     480
cttcgaagcc tcacagagat cttgaaagga ggggtcttga tccagcggaa ccccagctc     540 tgctaccagg acacgatttt gtggaaggac atcttccaca gaacaaccca gctggctctc     600
acactgatag acaccaaccg ctctcgggcc tgccaccct gttctccgat gtgtaagggc     660
tcccgctgct ggggagagag ttctgaggat tgtcagagcc tgacgcgcac tgtctgtgcc     720
ggtggctgtg cccgctgcaa ggggccactg cccactgact gctgccatga gcagtgtgct     780
gccggctgca gggcccccaa gcactctgac tgcctggcct gcctccactt caaccacagt     840
ggcatctgtg agctgcactg cccagccctg gtcacctaca cacagacac gtttgagtcc     900 atgcccaatc cgagggccg gtatacattc ggcgccagct gtgtgactgc ctgtccctac     960
aactaccttt ctacggacgt gggatcgggc gctggggca tggtccacca caggcaccgc    1020
agctcatcta ccaggagtgg cggtggggac ctgacactag gctggagcc ctctgaagag    1080 gaggccccca ggtctccact ggcaccctcc gaagggctg ctccgatgt atttgatggt    1140 gacctgggaa tggggcagc caaggggctg caaagcctcc ccacacatga ccccagccct    1200
ctacagcggt acagtgagga ccccacagta ccctgccct ctgagactga tggctacgtt    1260

-continued

| | | | | | |
|---|---|---|---|---|---|
| gcccccctga | cctgcagccc | ccagcctgaa | tatgtgaacc | agccagatgt | tcggccccag | 1320 |
| cccccttcgc | cccgagaggg | ccctctgcct | gctgcccgac | ctgctggtgc | cactctggaa | 1380 |
| agggccaaga | ctctctcccc | agggaagaat | ggggtcgtca | aagacgtttt | tgcctttggg | 1440 |
| ggtgccgtgg | agaacccga | gtacttgaca | ccccagggag | gagctgcccc | tcagccccac | 1500 |
| cctcctcctg | ccttcagccc | agccttcgac | aacctctatt | actgggacca | ggacccacca | 1560 |
| gagcgggggg | ctccacccag | caccttcaaa | gggacaccta | cggcagagaa | cccagagtac | 1620 |
| ctgggtctgg | acgtgccagc | ggccgcaccc | gcccgctcgc | ccagcccag | cacacagccc | 1680 |
| tgggagcatg | tgaatgccat | ccaggaggcc | cggcgtctcc | tgaacctgag | tagagacact | 1740 |
| gctgctgaga | tgaatgaaac | agtagaagtc | atctcagaaa | tgtttgacct | ccaggagccg | 1800 |
| acctgcctac | agacccgcct | ggagctgtac | aagcagggcc | tgcggggcag | cctcaccaag | 1860 |
| ctcaagggcc | ccttgaccat | gatggccagc | cactacaaac | agcactgccc | tccaaccccg | 1920 |
| gaaacttcct | gtgcaaccca | gattatcacc | tttgaaagtt | tcaaagaaa | cctgaaggac | 1980 |
| tttctgcttg | tcatcccctt | tgactgctgg | gagccagtcc | aggagggcgc | gccacccccg | 2040 |
| ccggcggccg | cacatcacca | tcaccatcac | | | | 2070 |